US008388936B2

(12) United States Patent
Kalyanaraman et al.

(10) Patent No.: US 8,388,936 B2
(45) Date of Patent: Mar. 5, 2013

(54) IN VIVO MITOCHONDRIAL LABELING USING POSITIVELY-CHARGED NITROXIDE ENHANCED AND GADOLINIUM CHELATE ENHANCED MAGNETIC RESONANCE IMAGING

(75) Inventors: Balaraman Kalyanaraman, Wauwatosa, WI (US); Joy Joseph, New Berlin, WI (US); Kathleen Marie Schmainda, Elm Grove, WI (US); Douglas Edward Prah, Milwaukee, WI (US); Marcos Lopez, Wauwatosa, WI (US); Micael J. Hardy, La Seyne sure mer (FR)

(73) Assignee: MCW Research Foundation, Inc., Milwaukee, WI (US)

( * ) Notice: Subject to any disclaimer, the term of this patent is extended or adjusted under 35 U.S.C. 154(b) by 626 days.

(21) Appl. No.: 12/390,929

(22) Filed: Feb. 23, 2009

(65) Prior Publication Data

US 2009/0214437 A1 Aug. 27, 2009

Related U.S. Application Data

(60) Provisional application No. 61/030,627, filed on Feb. 22, 2008.

(51) Int. Cl.
*A61B 5/055* (2006.01)
(52) U.S. Cl. ............... 424/9.33; 424/1.11; 424/1.53; 424/1.61; 424/9.3; 424/9.36; 556/20
(58) Field of Classification Search ............... 424/9.33
See application file for complete search history.

(56) References Cited

U.S. PATENT DOCUMENTS

| 4,142,102 | A | 2/1979 | Lange |
| 4,639,365 | A | 1/1987 | Sherry |
| 5,337,231 | A | 8/1994 | Nowak et al. |
| 2004/0033197 | A1 * | 2/2004 | Madar et al. ............... 424/9.1 |
| 2007/0066572 | A1 | 3/2007 | Balaraman et al. |
| 2007/0225255 | A1 | 9/2007 | Frohlich et al. |

FOREIGN PATENT DOCUMENTS

WO    WO 8911475 A1 * 11/1989

OTHER PUBLICATIONS

Yang et al. Inorganic chem. 2007, 8988-8997.*
Arbab, A., et al., Uptake of Technetium-99m-Tetrofosmin, Technetium-99m-MIBI and Thallium-201 in Tumor Cell Lines, J. Nucl. Med. 1996, 37(9):1551-1556.
Ballinger, J., et al., 99mTc-Tetrofosmin for Functional Imaging of P-glycoprotein Modulation in Vivo, J. Clin. Pharmacol. 2001, 41:39S-47S.
Berge, S., et al., Pharmaceutical Salts, J. Pharm. Sci. 1977, 66(1):1-19.
Brem, R., et al., Breast-specific Gamma Imaging as an Adjunct Imaging Modality for the Diagnosis of Breast Cancer, Radiology 2008, 247(3):651-657.
Brem, R., et al., Occult Breast Cancer: Scintimammography with High-Resolution Breast-specific Gamma Camera in Women at High Risk for Breast Cancer, Radiology 2005, 237:274-280.
Brem, R., et al., High-Resolution Scintimammography: A Pilot Study, J. Nucl. Med. 2002, 43(7):909-915.
Cooper, W., et al., H NMR Visible Lipids Are Induced by Phosphonium Salts and 5-Fluorouracil in Human Breast Cancer Cells, Magn. Reson. Med. 2001, 45:1001-1010.
Delmon-Moingeon, L., et al, Uptake of the Cation Hexakis(2-methoxyisobutylisonitrile)-Technetium-99m by Human Carcinoma Cell Lines in Vitro, Cancer Research 1990, 50:2198-2202.
Foster, P., et al., A New Therapeutic Strategy Against Hormone-Dependent Breast Cancer: The Preclinical Development of a Dual Aromatase and Sulfatase Inhibitor, Clin. Cancer Res. 2008, 14(20):6469-6477.
Hande, K., Clinical Applications of Anticancer Drugs Targeted to Topoisomerase II, Biochimica et Biophysica Acta 1998, 1400:173-184.
Haynes, D., et al., Occurrence of Pharmaceutically Acceptable Anions and Cations in the Cambridge Structural Database, J. Pharm. Sci. 2005, 94(10):2111-2120.
Hussain, R., et al., A Meta-Analysis of Scintimammography: An Evidence-Based Approach to its Clinical Utility, Nucl. Med. Commun. 2006, 27:589-594.
Jemal, A., et al., Cancer Statistics, 2004, CA Cancer J. Clin. 2004, 54:8-29.
Khalkhali, I., et al., 99mTc Sestamibi Breast Imaging for the Examination of Patients with Dense and Fatty Breasts: Multicenter Study, Radiology 2002, 222:149-155.
Khalkhali, I., et al., Scintimammography: The Complementary Role of Tc-99m Sestamibi Prone Breast Imaging for the Diagnosis of Breast Carcinoma, Radiology 1995, 196:421-426.
Kim, Y., et al., Effects of Targeting Moiety, Linker, Bifunctional Chelator, and Molecular Charge on Biological Properties of 64Cu-Labeled Triphenylphosphonium Cations, J. Med. Chem. 2008, 51:2971-2984.
Kroemer, G., Mitochondria in Cancer, Oncogene 2006, 25:4630-4632.
Liberman, M., et al., Breast Cancer Diagnosis by Scintimammography: A Meta-Analysis and Review of the Literature, Breast Canc. Res. Treat. 2003, 80:115-126.
Mathieu, I., et al., Inconclusive Triple Diagnosis in Breast Cancer Imaging: Is There a Place for Scintimammography?, J. Nucl. Med. 2005, 46(10):1574-1581.
Nandi, S., et al., Hormones and Mammary Carcinogenesis in Mice, Rats and Humans: A Unifying Hypothesis, Proc. Natl. Acad. Sci. USA 1995, 92:3650-3657.

(Continued)

*Primary Examiner* — Michael G Hartley
*Assistant Examiner* — Sean R Donohue
(74) *Attorney, Agent, or Firm* — Quarles & Brady LLP

(57) ABSTRACT

A system and method for acquiring MR imaging data from a subject includes administering positively-charged nitroxides or gadolinium chelates for in vivo mitochondrial labeling, acquiring MR imaging data from the subject, and reconstructing an image of the subject having enhanced contrast in areas including metabolic and/or mitotic activity.

2 Claims, 17 Drawing Sheets

OTHER PUBLICATIONS

Papantoniou, V., et al., The Potential Role of Calcitonin Gene-Related Peptide (CGRP) in Breast Carcinogenesis and Its Correlation with 99mTc-(V)DMSA Scintimammography, Am. J. of Clinical Oncology 2007, 30(4):420-427.

Parker, S., et al., Cancer Statistics, 1997, CA Cancer J. Clin. 1997, 47:5-27.

Piwnica-Worms, D., et al., Functional Imaging of Multidrug-Resistant P-Glycoprotein with an Organotechnetium Complex, Cancer Research 1993, 53:977-984.

Ross, M., et al., Lipophilic Triphenylphosphonium Cations as Tools in Mitochondrial Bioenergetics and Free Radical Biology, Biochemistry (Moscow) 2005, 70(2):222-230.

Sampalis, F., et al., International Prospective Evaluation of Scintimammography with 99mTechnetium Sestamibi, Am. J. Surgery 2003, 185:544-549.

Sheu, S., et al., Targeting Antioxidants to Mitochondria: A New Therapeutic Direction, Biochim. Biophys. Acta 2006, 1762:256-265.

Smith, R., et al., Targeting Coenzyme Q Derivatives to Mitochondria, Methods in Enzymology 2004, 382:45-67.

Smith, R., et al., Using Mitochondria-Targeted Molecules to Study Mitochondrial Radical Production and Its Consequences, Biochemical Society Transactions 2003, 31(6):1295-1299.

Spanu, A., et al., 99mTc-tetrofosmin SPET in the Detection of Both Primary Breast Cancer and Axillary Lymph Node Metastasis, Euro. J. Nucl. Med. 2001, 28(12):1781-1794.

Spanu, A., et al., The Role of Planar Scintimammography With High-Resolution Dedicated Breast Camera in the Diagnosis of Primary Breast Cancer, Clin. Nucl. Med. 2008, 33(11):739-742.

Sugiyama, S., Approaches that Mitigate Doxorubicin-Induced Delayed Adverse Effects on Mitochondrial Function in Rat Hearts; Liposome-Encapsulated Doxorubicin or Combination Therapy with Antioxidant, Biochemistry and Molecular Biology International 1995, 36(5):1001-1007.

Thompson, H., et al., Rat Models of Premalignant Breast Disease, J. Mamm. Gland Biol. Neoplas. 2000, 5 (4):409-420.

Wang, J., et al., 64Cu-Labeled Triphenylphosphonium and Triphenylarsonium Cations as Highly Tumor-Selective Imaging Agents, J. Med. Chem. 2007, 50:5057-5069.

United States Patent and Trademark Office, Office Action Summary and Detailed Action, U.S. Appl. No. 11/834,799, Apr. 29, 2010.

Applicants, Response to Election of Species Requirement, U.S. Appl. No. 11/834,799, May 11, 2010.

United States Patent and Trademark Office, Office Action Summary and Detailed Action, U.S. Appl. No. 11/834,799, Jun. 23, 2010.

Applicants, Response to Non-Final Office Action, U.S. Appl. No. 11/834,799, Oct. 25, 2010.

United States Patent and Trademark Office, Office Action Summary and Detailed Action, U.S. Appl. No. 11/834,799, Dec. 23, 2010.

Asin-Cayuela, et al., "Fine-tuning the hydrophobicity of a mitochondria-targeted antioxidant", FEBS Letters, 2004; 571:9-16.

Dhanasekaran, et al., "Mitochondria superoxide dismutase mimetic inhibits peroxide-induced oxidative damage and apoptosis: Role of mitochondrial superoxide", Free Radic Biol Med, 2005; 39(5):567-83.

Matsumoto, et al. "High-Resolution Mapping of Tumor Redox Status by Magnetic Resonance Imaging Using Nitroxides as Redox-Sensitive Contrast Agents", Clin. Cancer Res., 2006; 12(8):2455-2462.

Prah, et al. "In Vitro Mitochondrial Labeling using Mito-Carboxy Proxyl (Mito-CP) Enhanced Magnetic Resonance Imaging", Proc. Intl. Soc. Mag. Reson. Med. 15 (2007).

Prah, et al. "In Vivo Mitochondrial Labeling using Mito-Carboxy Proxyl (Mito-CP) Enhanced Magnetic Resonance Imaging", Proc. Intl. Soc. Mag. Reson. Med. 16 (2008).

Szewczyk, et al., "Mitochondria as a Pharmacological Target", Parmacological Reviews, 2002; 54(1):101-127.

Wang, S., et al., Doxorubicin Induces Apoptosis in Normal and Tumor Cells Via Distinctly Different Mechanisms, The Journal of Biological Chemistry, 2004, 279(24):25535-25543.

Wang, Y., et al., An Improved Synthesis of NHS-MAG3 for Conjugation and Radiolabeling of Biomolecules with 99mTc at Room Temperature, Nature Protocols, 2007, 2(4):972-978.

Applicant, Response to Dec. 23, 2010 Final Office Action and Section 1.132 Declaration, U.S. Appl. No. 11/834,799, Mar. 23, 2011.

United States Patent and Trademark Office, Office Action Summary and Detailed Action, U.S. Appl. No. 11/834,799, Oct. 13, 2011.

United States Patent and Trademark Office, Office Action Summary and Detailed Action, U.S. Appl. No. 12/394,581, Jul. 21, 2011.

Applicant, Preliminary Amendment and Reply to Jul. 21, 2011 Office Action, U.S. Appl. No. 12/394,581, Sep. 22, 2011.

United States Patent and Trademark Office, Office Action Summary and Detailed Action, U.S. Appl. No. 12/394,581, Mar. 13, 2012.

Applicant, Response to Mar. 13, 2012 Non-Final Office Action and Declaration Under 37 C.F.R. 1.132, U.S. Appl. No. 12/394,581, Sep. 13, 2012.

* cited by examiner

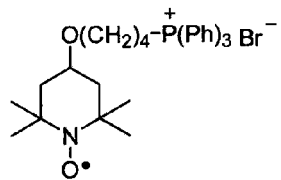

Mito-Tempol
(Tempo-4-oxotetramethylene
triphenylphosphonium bromide)

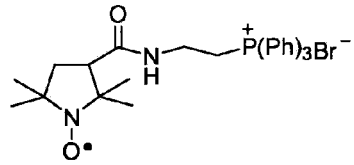

Mito-Proxyl amide
(Proxyl-3-carbonylaminodimethylene
triphenylphosphonium bromide)

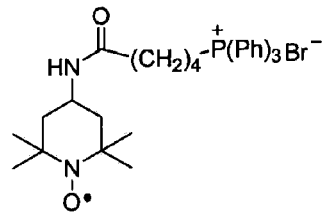

Mito-Tempol amide
(Tempo-4-aminocarbonyltetramethylene
triphenylphosphonium bromide)

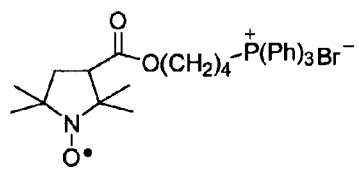

Mito-Proxyl ester
(Proxyl-3-carbonyloxotetramethylene
triphenylphosphonium bromide)

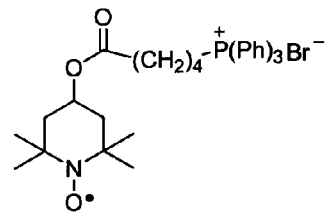

Mito-Tempol ester
(Tempo-4-oxocarbonyltetramethylene
triphenylphosphonium bromide)

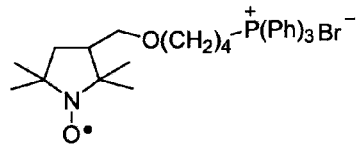

Mito-Proxyl ether
(Proxyl-3-methyleneoxotetramethylene
triphenylphosphonium bromide)

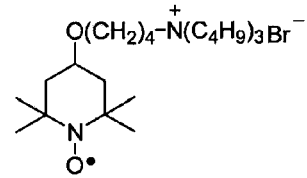

Tributylalkylammonium Tempol ether
(Tempo-4-oxotetramethylene
tributylammonium bromide)

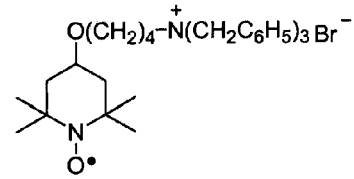

TribenzylalkylammoniumTempol ether
(Tempo-4-oxotetramethylene
tribenzylammonium bromide)

Fig. 13

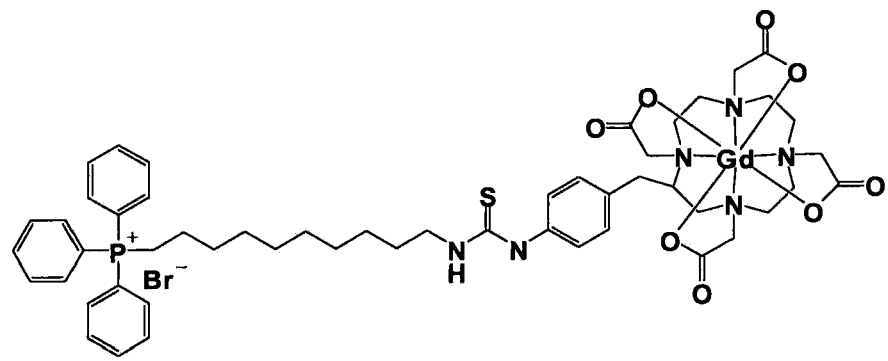
Mito-Gd-DOTA
Chemical Formula: $C_{52}H_{65}BrGdN_6O_8PS$
Molecular Weight: 1202.30
$T_1 = 4.43$ mM$^{-1}$ s$^{-1}$
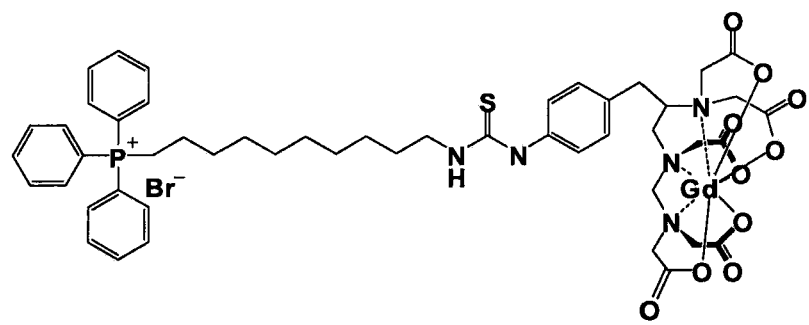
Mito-Gd-DTPA
Chemical Formula: $C_{50}H_{60}BrGdN_5O_{10}PS$
Molecular Weight: 1191.23
Fig. 14

A
B
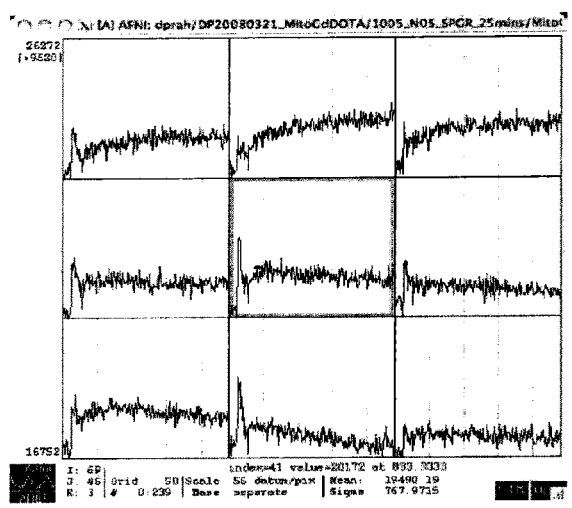
Fig. 15

IN VIVO MITOCHONDRIAL LABELING USING POSITIVELY-CHARGED NITROXIDE ENHANCED AND GADOLINIUM CHELATE ENHANCED MAGNETIC RESONANCE IMAGING

CROSS-REFERENCE TO RELATED APPLICATIONS

This application claims the benefit of U.S. Application No. 61/030,627, filed on Feb. 22, 2008, which is incorporated by reference herein in its entirety. The present application describes technology similar to that disclosed in commonly owned U.S. application Ser. No. 12/394,581, titled "$^{99m}$Tc-Labeled Triphenylphosphonium Derivative Contrasting Agents and Molecular Probes for Early Detection and Imaging of Breast Tumors."

STATEMENT REGARDING FEDERALLY SPONSORED RESEARCH OR DEVELOPMENT

This invention was made with United States government support awarded by: NIH/NINDS NS39958-07; NIH/NCI RO1 CA082500; NIH/NHLBI RO1 HL073056-06; and NIH/NCI 1R21CA109280. The United States government has certain rights in this invention.

FIELD OF THE INVENTION

The present invention relates generally to the field of magnetic resonance imaging. More particularly, the invention is directed to in vivo mitochondrial labeling using positively-charged nitroxide enhanced or gadolinium chelate enhanced magnetic resonance imaging.

BACKGROUND OF THE INVENTION

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment Mz is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) that is in the x-y plane and is near the Larmor frequency, the net aligned moment, Mz, may be rotated, or "tipped" into the x-y plane to produce a net transverse magnetic moment Mt, which is rotating, or spinning, in the x-y plane at the Larmor frequency. The practical value of this phenomenon resides in the signal that is emitted by the excited spins after the excitation signal $B_1$ is terminated.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MRI signals is received using a receiver coil. The MRI signals are then digitized and processed to reconstruct the image using one of many well-known reconstruction techniques.

These signals can be decomposed into directional components. The relaxation time T1 is the time required for the z component of M to return to 63 percent of its original value following excitation. It is also referred to as spin-lattice relaxation or longitudinal relaxation. The relaxation time T2 is the time required for the transverse component of M to decay to 37 percent of the initial value. It is also know as the spin-spin relaxation time or transverse relaxation time.

The ability to depict anatomy and pathology using MRI is dependent on the contrast, or difference in signal intensity between the target and background tissue. In order to maximize contrast, it is necessary to suppress the signal intensities of the background tissues. Substances can be contrasted in an MR image by the differences in either their T1 or T2 characteristics.

Contrast agents can be used to modify the T1 or T2 characteristics in vivo. The specific modification in contrast caused by a given contrast agent is due to an effect of shortening the relaxation time T1 and/or T2 of the hydrogen nuclei. If the contrast agent reduces T1, a T1 hypersignal is observed in the reconstructed image. On the other hand, if the contrast agent shortens T2, a reduction in the T2 and T2* signal will be observed in the reconstructed image.

One very common application of MR imaging is in vivo screening for tumors. However, distinguishing a tumor from surrounding tissue can, at times, be difficult. That is, it is often difficult to maximize the signal intensity received from the tumor while suppressing the signal intensities received from the surrounding tissue.

Also, generally speaking, MR imaging is advantageous in performing anatomical analysis. That is, unlike other imaging modalities, such as positron emission tomography, MR imaging is not as readily suited for functional imaging. To perform functional analysis using MR imaging, a contrast agent is typically employed. For example, when performing functional MRI (fMRI) of the brain, oxygen is typically employed as a contrast agent using the BOLD method. On the other hand, when attempting to image arterial or venous flow, a contrast agent such as gadolinium is utilized. In either case, the functional imaging is achieved by monitoring the presence or absence of the contrast agent using MR imaging. However, there are many functional processes within the body that cannot be imaged using traditional contrast agents.

Therefore, it would be desirable to have a system and method for enhancing the contrast of specific structures, such as tumors. Furthermore, it would be desirable to have a system and method for imaging functional processes in vivo that cannot otherwise be imaged using traditional functional MR imaging.

SUMMARY OF THE INVENTION

The present invention overcomes the aforementioned drawbacks by providing a system and method for enhancing the contrast of processes or specific structures, such as tumors, during an MR imaging process. Specifically, a contrast agent is provided that is designed to target mitochondria as a marker for metabolic and/or mitotic activity. Accordingly, the contrast of pathologies, such as tumors, where metabolic activity is significantly increased, is enhanced during MR imaging. Furthermore, functional processes earmarked by metabolic and/or mitotic activity can be readily identified during an MR imaging process using the contrast agent.

Contrast agents particularly useful in methods according to the present invention are mitochondria-targeted nitroxides and mitochondria-targeted gadolinium (III) chelate complexes. Due to their paramagnetic properties, the nitroxide or gadolinium chelate moieties exhibit $T_1$-contrast enhancement, making the molecules useful as MR contrast agents. Mitochondria-targeted contrast agents molecules according to the invention further include a mitochondria targeting moiety, preferably a triphenylphosphonium group or a benzyl ammonium group.

Preferred mitochondria-targeted nitroxides for use in the present methods additionally contain ether, amide, or ester linkages to couple the mitochondria targeting moiety and the nitroxide. Thus, the preferred mitochondria-targeted nitroxides are positively charged nitroxide ethers, positively charged nitroxide esters or positively charged nitroxide amides. Suitable positively charged nitroxides include, but are not limited to, Mito-Tempol ether, Mito-Tempol ester, Mito-Tempol amide, Mito-CP, Mito-Tempamide, Mito-Proxyl ether, Mito-Proxyl ester, Mito-Proxyl amide, Tributylalkylammonium Tempol ether and Tribenzyalkylammonium Tempol ether. A particularly preferred molecule for use in methods according to the invention is Mito-CP.

Preferred mitochondria-targeted gadolinium chelates for use in the present methods contain a coordination complex consisting of a gadolinium (III) ion bound to a hexadentate, heptadentate, octadentate, or nonadentate organic chelating agent. Examples of such chelating agents include 1,4,7,10-tetrazacyclododecane-N,N',N'',N'''  tetracetate  (DOTA); diethylenetriaminepentaacetate (DTPA); 1,4,7-triazacyclononane-N,N',N''-triacetate (NOTA); 1,5,9-triazacyclododecane-N,N',N''-triacetate (DOTRA); 1,4,8,11-tetraazacyclotetradecane-N,N',N'',N'''-tetraacetate (TETA); and salts thereof.

The mitochondria-targeted gadolinium chelate contrast agent molecules of the present invention further contain a mitochondria targeting moiety such as a triphenylphosphonium group or a benzyl ammonium group. The preferred mitochondria targeting moiety is a triphenylphosphonium group.

More preferred mitochondria-targeted gadolinium chelates additionally contain phenylthiocarbamide linkages to couple the mitochondria targeting moiety and the gadolinium chelates. In some preferred embodiments, the linkage may additionally contain an alkyl chain, most preferably a ten carbon unbranched alkyl chain. Suitable mitochondria-targeted gadolinium chelates for use in the present methods include, but are not limited to, Mito-Gd-DOTA and Mito-Gd-DTPA. A particularly preferred molecule for use in methods according to the invention is Mito-Gd-DOTA.

Furthermore, it can be appreciated that the present invention also provides novel mitochondria-targeted contrast agents including certain compounds having the formula:

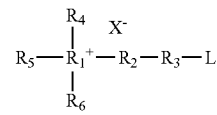

wherein L is a paramagnetic metal selected from Cr, Mn, Fe, Co, Ni, Cu, Pr, Nd, Sm, Y, Gd, Tb, Dy, Nd, Pm, Ho, Sm, Tm, Eu, Yb, Lu or Er, wherein $R_1$ is S, N or P, wherein $R_2$ is a branched or straight chain, saturated or unsaturated, substituted or unsubstituted $C_{1-25}$ group, wherein $R_3$ is a branched or straight chain, saturated or unsaturated, substituted or unsubstituted organic chelating moiety comprising one or more of carboxyl, amine, amide, ester, alcohol or thiol, wherein $R_4$, $R_5$ or $R_6$ are the same or independently a straight or branched, saturated or unsaturated, substituted or unsubstituted $C_{1-10}$ alkyl or cycloalkyl, substituted or unsubstituted phenyl, or substituted or unsubstituted benzyl, and, wherein $X^-$ is $Cl^-$, $I^-$, $Fl^-$ or another salt-forming counterion, or a solvate or hydrate thereof. In preferred compounds, $R_2$ is a branched or straight chain, saturated or unsaturated, substituted or unsubstituted $C_{4-10}$ alkyl. The organic chelating moiety is preferably a hexadentate, heptadentate, octadentate, or nonadentate organic chelating moiety, in certain embodiments selected from the group consisting of: 1,4,7,10-tetrazacyclododecane-N,N',N'',N''' tetracetate (DOTA); diethylenetriaminepentaacetate (DTPA); 1,4,7-triazacyclononane-N,N',N''-triacetate (NOTA); 1,5,9-triazacyclododecane-N,N',N''-triacetate (DOTRA); 1,4,8,11-tetraazacyclotetradecane-N,N',N'',N'''-tetraacetate (TETA); and salts thereof. The preferred paramagnetic metal L is the metal Gd. One preferred mitochondria-targeted contrast agent is the compound Mito-Gd-DOTA having the structure:

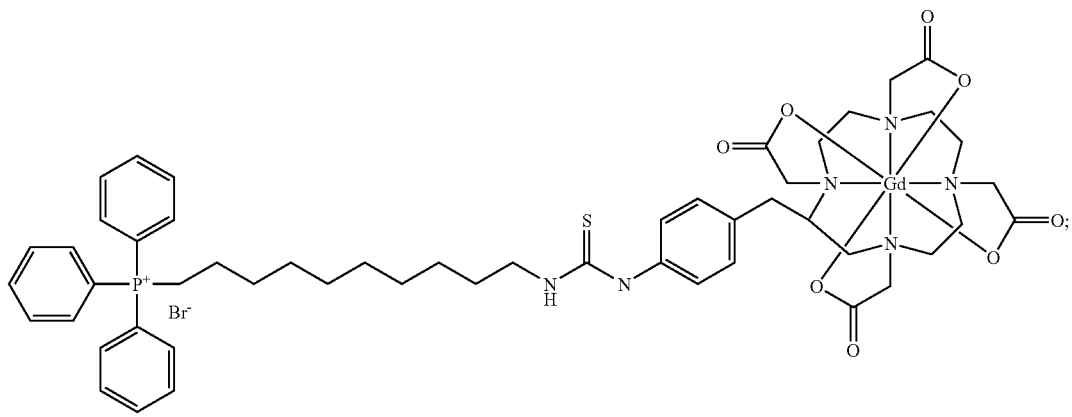

An alternative mitochondria-targeted contrast agent, also preferred, is the compound Mito-Gd-DTPA having the structure:

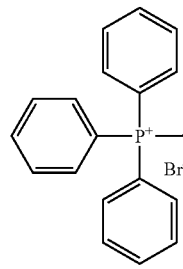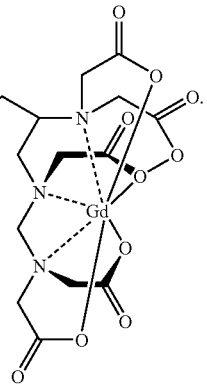

In certain embodiments, the compounds according to the invention are provided in the form of an injectable dosage. Such compositions include one or more of the compounds described and claimed herein along with a pharmaceutically suitable injectable carrier system.

The invention further encompasses compounds made by the steps of providing a compound having the formula:

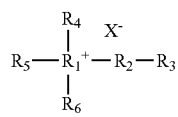

wherein $R_1$ is S, N or P, wherein $R_2$ is branched or straight chain, saturated or unsaturated, substituted or unsubstituted $C_{1-25}$ group, wherein $R_3$ is a branched or straight chain, saturated or unsaturated, substituted or unsubstituted organic chelating moiety comprising one or more of carboxyl, amine, amide, ester, alcohol or thiol, wherein $R_4$, $R_5$ or $R_6$ are the same or independently a straight or branched, saturated or unsaturated, substituted or unsubstituted $C_{1-10}$ alkyl or cycloalkyl, substituted or unsubstituted phenyl, or substituted or unsubstituted benzyl, and, wherein $X^-$ is $Cl^-$, $I^-$, $Fl^-$ or another salt-forming counterion, or a solvate or hydrate thereof, and chelating the compound by contacting the compound with a paramagnetic metal selected from Cr, Mn, Fe, Co, Ni, Cu, Pr, Nd, Sm, Y, Gd, Tb, Dy, Nd, Pm, Ho, Sm, Tm, Eu, Yb, Lu or Er.

Of course, the invention contemplates methods of in vivo MR imaging a target area of a subject comprising the steps of: (a) administering a compound having one of the structures described and claimed herein to the subject; (b) applying a pulse sequence selected to acquire MR imaging data from the target area of the subject; and (c) reconstructing an image of the target area of the subject having enhanced contrast in areas of at least one of metabolic and mitotic activity.

While the invention defined by the appended claims is susceptible to various modifications and alternative forms, specific embodiments thereof have been shown by way of example in the drawings and are herein described in detail. It should be understood, however, that the description of specific embodiments is not intended to limit the invention to the particular forms disclosed, but on the contrary, the intention is to cover all modifications, equivalents and alternatives falling within the spirit and scope of the invention as defined by the appended claims.

BRIEF DESCRIPTION OF THE DRAWINGS

The invention will be better understood when consideration is given to the following detailed description thereof. Such detailed description makes reference to the following drawings, wherein:

FIG. 13 shows the chemical structures of the positively charged nitroxides Mito-Tempol ether, Mito-Tempol ester, Mito-Tempol amide, Mito-Proxyl ether, Mito-Proxyl ester, Mito-Proxyl amide, Tributylalkylammonium Tempol ether and Tribenzyalkylammonium Tempol ether.

FIG. 14 shows the chemical structures of Mito-Gadolinium (III)-1,4,7,10-tetraazacyclododecane-N,N',N",N"'-tetraacetic acid (Mito-Gd-DOTA) and Mito-Gadolinium (III)-diethylenetriaminepentaacetic acid (Mito-Gd-DTPA).

FIG. 15A shows a dynamic time series of Mito-Gd-DOTA uptake from within a C6 glioma (brain tumor). FIG. 15B shows post contrast MRI images taken 40 minutes after injection with Mito-Gd-DOTA.

DETAILED DESCRIPTION OF THE INVENTION

The present invention relates to the inventors' observation that certain mitochondria targeted nitroxides and mitochondria-targeted gadolinium (III) chelate complexes are useful contrast agents in in vivo imaging applications.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are now described.

Figure 1:
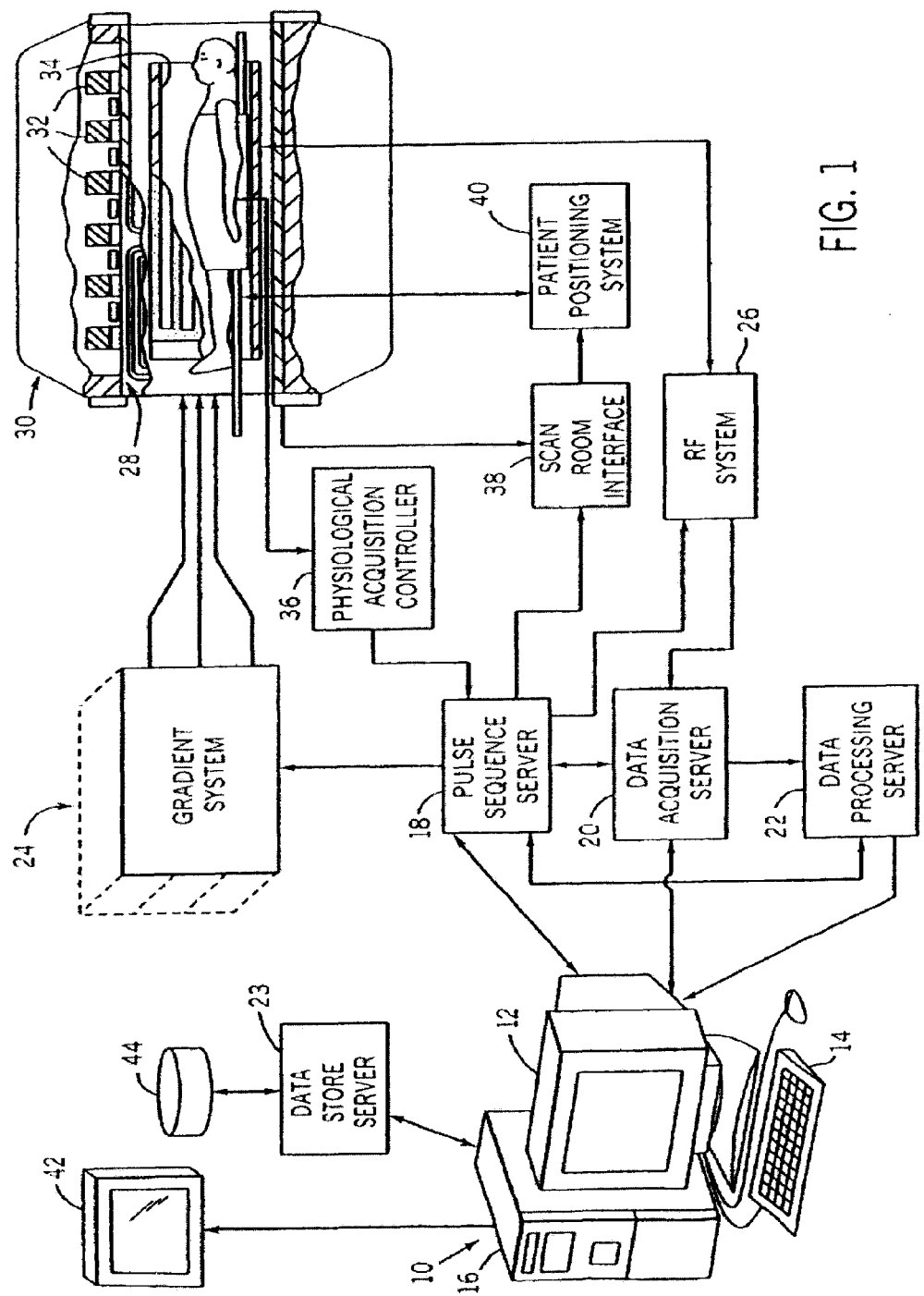
FIG. 1 is a block diagram of an MRI system for use with the present invention.

Referring particularly to FIG. 1, the invention is employed with an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system.

The workstation 10 is coupled to four servers: a pulse sequence server 18; a data acquisition server 20; a data processing server 22, and a data store server 23. In the one embodiment, the data store server 23 is performed by the workstation processor 16 and associated disc drive interface circuitry. The remaining three servers 18, 20 and 22 are performed by separate processors mounted in a single enclosure and interconnected using a backplane bus. The pulse sequence server 18 employs a commercially available microprocessor and a commercially available communication controller. The data acquisition server 20 and data processing server 22 both employ commercially available microprocessors and the data processing server 22 further includes one or more array processors based on commercially available parallel vector processors.

The workstation 10 and each processor for the servers 18, 20 and 22 are connected to a serial communications network. This serial network conveys data that is downloaded to the servers 18, 20 and 22 from the workstation 10 and it conveys tag data that is communicated between the servers and between the workstation and the servers. In addition, a high speed data link is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24, which excites gradient coils in an assembly 28 to produce the magnetic field gradients Gx, Gy, and Gz used for position encoding NMR signals. The gradient coil assembly 28 forms part of a magnet assembly 30, which includes a polarizing magnet 32 and a whole-body RF coil 34.

The RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered, and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase, and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the RF coil to which it is connected and a quadrature detector which detects and digitizes the I and Q quadrature components of the received NMR signal. The magnitude of the received NMR signal may thus be determined at any sampled point by the square root of the sum of the squares of the I and Q components: $M=\sqrt{I^2+Q^2}$, and the phase of the received NMR signal may also be determined: $\phi=\tan^{-1} Q/I$.

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is the pulse sequence server 18 includes hardware elements that are operated with program instructions that are executed in a timely manner by run-time programs. The description components for a scan prescription are downloaded from the workstation 10 in the form of objects. The pulse sequence server 18 contains programs that receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans, the data acquisition server 20 does little more than pass the acquired NMR data to the data processor server 22. However, in scans that require information derived from acquired NMR data to control the further performance of the scan, the data acquisition server 20 is programmed to produce such information and convey it to the pulse sequence server 18. For example, during prescans, NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agents. In all these examples the data acquisition server 20 acquires NMR data and processes it in real-time to produce information which is used to control the scan.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, and the like.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real-time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Using the above-described MRI system, a method of medical imaging can be performed using a $T_1$-targeted contrast agent. A wide variety of processes are contemplated for imaging tumors or other areas of high metabolic and/or mitotic activity. Furthermore, a variety of processes are contemplated for performing functional imaging processes using the above-described MRI system including, but not limited to, assay of tissue redox status by dynamic $T_1$-weighted imaging.

One group of contrast agents useful in the present invention are mitochondria-targeted nitroxides. Nitroxide radicals, due to a single unpaired electron, exhibit $T_1$-contrast enhancement. Nitroxides have also been shown to exhibit $T_1$ contrast enhancement in vivo. As used herein, the term "nitroxide" refers to any five-membered or six-membered ring having a stabilized nitroxide moiety. The term "mitochondria-targeted nitroxide" refers to any nitroxide conjugated to a molecule that increases its lipid bilayer permeability. Such molecules include, but are not limited to, a triphenylphosphonium group or a benzyl ammonium group.

The nitroxide moiety is generally coupled to the molecule that increases lipid bilayer permeability via an ether, amide or ester linkage. This linkage may be of varying chain length with longer chain lengths increasing the mitochondria-targeted nitroxide's hydrophobic character. Accordingly, the mitochondria-targeted nitroxide is generally a positively charged nitroxide ether, a positively charged nitroxide ester or a positively charged nitroxide amide.

In specific embodiments, the mitochondria-targeted nitroxide is Mito-Tempol ether, Mito-Tempol ester, Mito-Tempol amide, Mito-CP, Mito-Tempamide, Mito-Proxyl ether, Mito-Proxyl ester, Mito-Proxyl amide, Tributylalkylammonium Tempol ether, or Tribenzyalkylammonium Tempol ether (see FIG. 13). The syntheses of the specific molecules described herein were previously described in U.S. patent application Ser. No. 11/520,191, filed Sep. 13, 2006, and Dhanasekaran, et al., *Free Radic Biol Med*, 2005. 39(5): p. 567-83, both of which are incorporate herein by reference in their entireties. Accordingly, mitochondria-targeted nitroxides useful in the invention may be based on, e.g., 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6tetramethyl-1-piperidinyloxy (Tempamine), 3-Aminomethyl-PROXYL, 3-CyanoPROXYL, 3-Carbamoyl-PROXYL, 3-Carboxy-PROXYL, and 4-0xo-TEMPO. Molecules such as TEMPO, for example, can also be substituted, typically in the 4 position, e.g., 4-amino, 4-(2 bromoacetamido), 4-(ethoxyfluorophosphonyloxy), 4-hydroxy, 4-(2-iodoacetamido), 4 isothiocyanato, 4-maleimido, 4-(4-nitrobenzoyloxyl), 4-phosphonooxy, and derivatives thereof.

Figure 2:
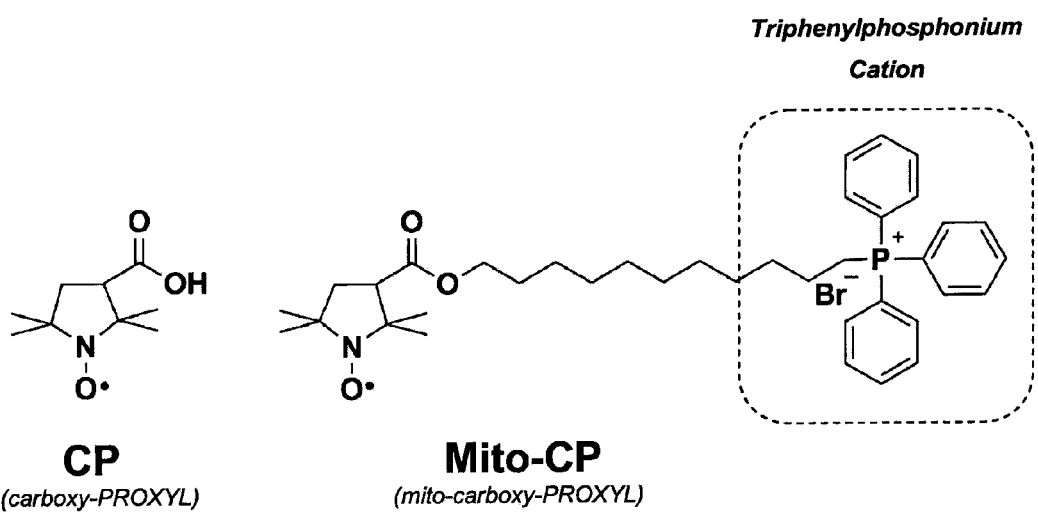
FIG. 2 shows the chemical structures of Carboxy-Proxyl (CP) and Mito-Carboxy-Proxyl (Mito-CP).

The structure of one preferred mitochondria-targeted nitroxide, Mito-CP, is depicted in FIG. 2, along with the structure of the untargeted nitroxide, CP. Mito-CP has been shown to preferentially target mitochondria. Both CP and Mito-CP molecules are paramagnetic, due the single unpaired electron delocalized over the nitrogen oxygen bond, which allows detection by both MR and EPR. Alone, the 5-membered nitroxide ring, CP, lacks the ability to accumulate selectively within functional mitochondria. However, when the CP is covalently bound to triphenylphosphonium with 11-carbon linkage, Mito-CP, mitochondrial accumulation occurs. While no one theory of operation is adopted herein, Mito-CP is most likely taken up by mitochondria because: (1) lipophilic cations, such as the triphenylphosphonium cation, distribute their charge over a large surface area allowing them to penetrate the lipid bilayers; and (2) uptake of lipophilic ions through the lipid bilayers is increased 10-fold for every 61.5 mV difference in the membrane potential. This would apparently explain the uptake of Mito-CP across the plasma membrane (30-60 mV) and across the mitochondria membrane (150-180 mV).

A second group of contrast agents useful in the present invention are mitochondria-targeted gadolinium (III) chelate complexes. Gadolinium, due to its seven unpaired electrons, has strong paramagnetic properties. Its large magnetic moment, which efficiently relaxes magnetic nuclei, causes it to exhibit $T_1$-contrast enhancement. Because gadolinium is toxic to animals, its use in animals for contrast enhancement is limited to compounds such as gadolinium complexes or chelates that are excreted without releasing the toxic gadolinium ions. See U.S. Pat. No. 4,639,365, which is incorporated by reference herein. A number of gadolinium chelates have been shown to exhibit $T_1$ contrast enhancement in vivo.

As used herein, the term "gadolinium chelate" refers to a coordination complex consisting of a gadolinium (III) ion bound to a hexadentate, heptadentate, octadentate, or nonadentate organic chelating agent. Examples of such organic chelating agents include, without limitation, 1,4,7,10-tetrazacyclododecane-N,N',N'',N''' tetracetate (DOTA); diethylenetriaminepentaacetate (DTPA); 1,4,7-triazacyclononane-N,N',N"-triacetate (NOTA); 1,5,9-triazacyclododecane-N,N',N"-triacetate (DOTRA); 1,4,8,11-tetraazacyclotetradecane-N,N',N",N'"-tetraacetate (TETA); and salts thereof. The term "mitochondria-targeted gadolinium chelate" refers to any gadolinium chelate conjugated to a molecule that increases its lipid bilayer permeability. Such molecules include, but are not limited to, a triphenylphosphonium group or a benzyl ammonium group.

The molecule that increases lipid bilayer permeability is generally coupled to the gadolinium chelate moiety via a carbon chain attached to a phenylthiocarbamide (phenylthiourea), thiocarbamide (thiourea), thioamide, ether, amide or ester linkage. The linkage is attached to the gadolinium chelate moiety, either directly or through an additional short carbon chain. The first carbon chain, extending from the molecule that increases lipid bilayer permeability to the linkage, may be of varying chain lengths (preferably from two to eleven carbons, more preferably ten carbons), with longer chain lengths increasing the mitochondria-targeted gadolinium chelate's hydrophobic character.

A preferred mitochondria-targeted gadolinium chelate is generally a positively charged triphenylphosphonium phenylthiocarbamide gadolinium chelate, wherein the triphenylphosphonium group is attached to a ten carbon chain coupled to a phenylthiocarbamide linking group, which is attached through an additional one-carbon chain to a gadolinium chelate moeity. In specific embodiments, the mitochondria-targeted gadolinium chelate is Mito-Gd-DOTA or Mito-Gd-DOTA (see FIG. 14). The syntheses of these specific molecules is described herein at Example 8.

For in vivo imaging applications, mitochondria-targeted nitroxides or mitochondria-targeted gadolinium chelates are administered intravenously or intraperitoneally, alone or in combination with a pharmaceutically-acceptable carrier. Alternatively, the compounds may be administered orally where the target area to be imaged is associated with the upper digestive tract, particularly the mouth, pharynx or esophagus. Mitochondria-targeted nitroxides and mitochondria-targeted gadolinium chelates are generally stable in aqueous solutions at a pH of about 7.0.

Dosages of mitochondria-targeted nitroxide suitable for in vivo imaging applications are in a range of about 0.1 mg/kg to about 100 mg/kg body weight. It is noted that the number of doses a subject receives, the time allowed between doses and the length of time a subject receives mitochondria-targeted nitroxides will depend upon, for example, the subject's body weight and duration of imaging procedure.

In another embodiment, the invention includes the disclosed mitochondria-targeted gadolinium (III) chelate complex molecules. Although a number of gadolinium chelates are known, Applicants for the first time have synthesized the disclosed mitochondria-targeted gadolinium chelates. The preferred molecules of this embodiment of the invention are triphenylphosphonium phenylthiocarbamide gadolinium chelates, wherein the triphenylphosphonium group is attached to a ten carbon chain coupled to a phenylthiocarbamide linking group, which is attached through an additional one-carbon chain to a gadolinium chelate moeity. In specific embodiments, the mitochondria-targeted gadolinium chelate is Mito-Gd-DOTA or Mito-Gd-DPTA (see FIG. 14). The syntheses of these specific molecules is described herein at Example 8.

As used herein, a "salt-forming counterion" may be a pharmaceutically suitable (i.e., pharmaceutically acceptable) salt including, but not limited to, acid addition salts formed by mixing a solution of the instant compound with a solution of a pharmaceutically acceptable acid. The pharmaceutically acceptable acid may be hydrochloric acid, methanesulphonic acid, fumaric acid, maleic acid, succinic acid, acetic acid, benzoic acid, oxalic acid, citric acid, tartaric acid, carbonic acid or phosphoric acid. Various pharmaceutically acceptable salts are well known in the art and may be used with the instant compound such as those disclosed in Berge SM et al., "Pharmaceutical Salts." *J. Pharm. Sci.* 66:1-19 (1977) and Haynes DA et al., "Occurrence of pharmaceutically acceptable anions and cations in the Cambridge Structural Database," *J. Pharm. Sci.* 94:2111-2120 (2005), which are hereby incorporated herein by reference. For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

As used herein, "hydrates" of the instant compound may be a pharmaceutically suitable (i.e., pharmaceutically acceptable) hydrate that is a compound formed by the addition of water or its elements to a host molecule (e.g., the free form version of the compound) including, but not limited to, monohydrates, dihydrates, etc.

As used herein, the terms "injectable" and "infusion dosage forms" (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

A parenteral or injectable carrier system according to the invention includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The invention will be more fully understood upon consideration of the following non-limiting Examples.

EXAMPLES

Example 1

Materials and Methods

All chemical and reagents were obtained from Sigma-Aldrich (Milwaukee, Wis.) unless otherwise noticed. All reagents were used as received without further purification. All cell culture materials and buffers were obtained from Invitrogen (Grand Island, N.Y.).

Synthesis of Mito-CP. Mito-CP, (11-(3-carboxy-2,2,5,5-tetramethyl-1-pyrrolidinyloxy)-undecyl)-triphenylphosphonium bromide was synthesized as described previously (Dhanasekaran, et al. at *Free Radic Biol Med*, 2005. 39(5): p. 567-8).

Cell Culture. MCF7, MDA-MB-231 and MCF10-A cells were obtained from the American Type Culture Collection (ATCC) and cultured at 37° C. in humidified 95% air/5% $CO_2$. MCF7 cells were maintained in MEM-alpha medium containing 10% FBS, L-glutamine (4 mM), penicillin (100 μg/ml), streptomycin (100 μg/ml), non-essential amino acids and sodium pyruvate. MDA-MB-23 were grown in Dulbecco's Modified Eagle's medium (DMEM) containing 10% FBS, L-glutamine (4 mM), penicillin (100 μg/ml), and streptomycin (100 μg/ml). MCF10-A cells were maintained in F-12 media supplemented with 20% FHS, hydrocortisone, cholera toxin, penicillin, streptomycin, and endothelial cell growth factor (ECGF). Typically, the day of the treatment, various concentrations of the nitroxides were added to the cells directly in the media.

T1 Relaxivity at 1.5 Tesla. The longitudinal relaxivities of CP and Mito-CP were determined using a LX 1.5 T GE Scanner (GE, Waukesha, Wis.) using an 8-channel head rf coil. Solutions of CP and Mito-CP were diluted with Dulbecco's Phosphate Buffered Saline (DPBS) to the following concentrations: 5.0 μM, 10.0 μM, 20.0 μM, 50.0 μM, 100.0 μM, 200.0 μM, 300.0 μM, 500.0 μM, 700.0 μM, 1.0 mM, 2.0 mM, 5.0 mM, 10.0 mM, and 20.0 mM. Longitudinal relaxation times ($T_1$) for each solution and relaxivities ($R_1$) for CP and Mito-CP were calculated using images from a standard spin echo sequence (TE=14 msec, TR=10 sec) at various inversion times (TI=50, 125 msec incrementing by 125 msec to 3500 msec and 4000 msec).

T1 Relaxivity at 3.0 Tesla. The longitudinal relaxivities of CP and Mito-CP were determined using a Signa 3.0 T GE Scanner (GE, Waukesha, Wis.) using a custom rf quadrature coil. Solutions of CP and Mito-CP were diluted with Dulbecco's Phosphate Buffered Saline (DPBS) to the following concentrations: 1.0 μM, 10.0 μM, 100.0 μM, 1.0 mM, 10.0 mM, and 20.0 mM. Longitudinal relaxation times ($T_1$) for each solution and relaxivities ($R_1$) for CP and Mito-CP were calculated using images from a standard spin echo sequence (TE=9 msec, TR=15 sec) at various inversion times (TI=100 msec incrementing by 100 msec to 4000 msec and 50, 150, 1050, 1150 msec).

T1 Relaxivity at 9.4 Tesla. Both solutions were diluted with Dulbecco's Phosphate Buffered Saline (DPBS) to the following concentrations: 1.0 mM, 10.0 mM, 100.0 mM, 1.0 mM, 10.0 mM, and 20.0 mM. Longitudinal relaxation times ($T_1$) for each solution and relaxivities ($R_1$) for CP and Mito-CP were calculated using a standard spin echo sequence (TE=9 msec, TR=15,000 msec) at various inversion times (TI=100 msec incrementing by 100 msec to 4000 msec and 50, 150, 1050, 1150 msec).

Experimental setup for in vivo rat nitroxides concentration measurements in blood with X-band EPR. Each anesthetized rat was given heparin, placed on a warming pad, and positioned above the EPR cavity. A femoral arterial line (PE50 tubing) was fed down through the EPR cavity and connected to the femoral venous line with a PVC couple. After the unit was tuned, a nitroxide bolus was given via the tail vein catheter and repeated acquisitions (every 86 s) of the EPR spectrum were simultaneously initiated. Identical EPR parameters were maintained within and among all rats throughout the entire study.

Example 2

Cell Viability Assay

The MTT assay (Sigma-Aldrich, Milwaukee, Wis.) was used to measure cell survival using quantitative colorimetry (λ=570 nm). This assay is based on the capacity of mitochondrial dehydrogenases to reduce MTT to form the insoluble formazan product. Cells were plated in 12-well plates and treated at pre-confluency with Mito-CP and CP (0-30 μM) in their respective media for 48 h. The culture media was removed after treatment, washed gently with DPBS and MTT (5 mg/ml in media) was added to each well, following incubation of the plates for 1 h at 37° C. The MTT solution was removed and the formazan product in each well was dissolved with dimethyl sulfoxide (DMSO). The optical density of each well was measured using an Agilent 8453 UV-Vis spectrometer at 570 nm.

Figure 3:
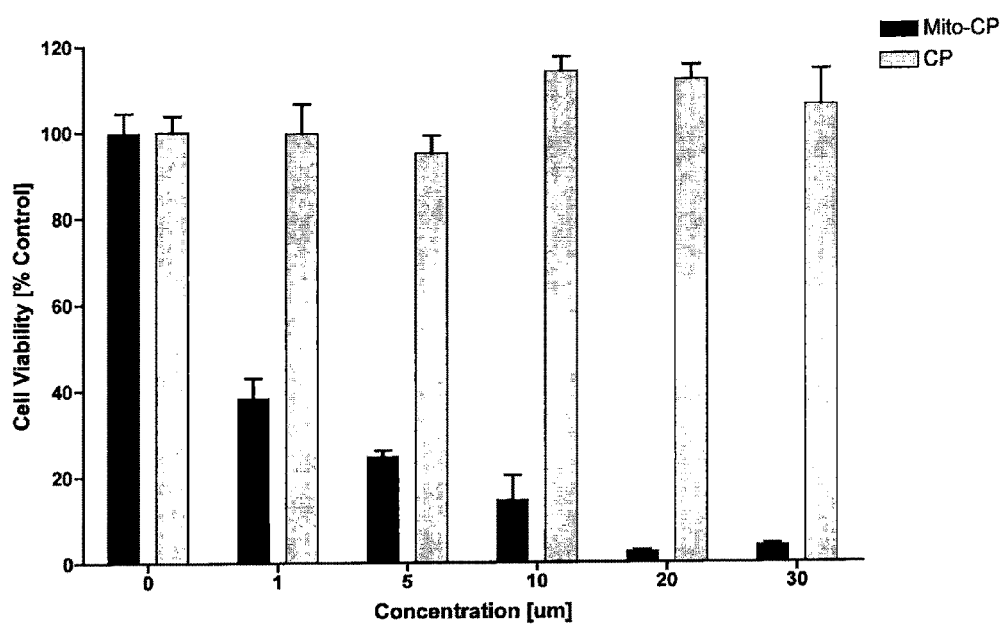
FIG. 3 shows cell viability data obtained from MTT assay results.

MCF7, MDA-MB-231 and non-tumorigenic MCF10-A were grown to pre-confluency and treated with either Mito-CP or parent compound CP (1-30 uM) for 48 h and cell viability was measured using the MTT assay. FIG. 3 shows that Mito-CP induced cancer cell apoptosis while the parent compound CP did not. Mito-CP or CP had no influence inducing apoptosis in normal MCF10-A breast epithelial cells. These results suggest the differential signaling and action mechanisms of Mito-CP and CP in breast cancer cells and normal epithelial cells.

Example 3

Relaxivities of CP and Mito-CP

The longitudinal relaxivities of other nitroxides have been approximate 0.2 mmol$^{-1}$ s$^{-1}$. In order to assess the longitudinal relaxivity of CP and Mito-CP, concentrations were prepared with the expectation of this relaxivity. Two separate initial solutions of CP and Mito-CP were prepared. Longitudinal relaxivities were determined for both CP and Mito-CP at three field strengths. Relaxivities were obtained from non-linear fits of standard spin echo inversion recovery images calculated using Matlab.

Figure 4:
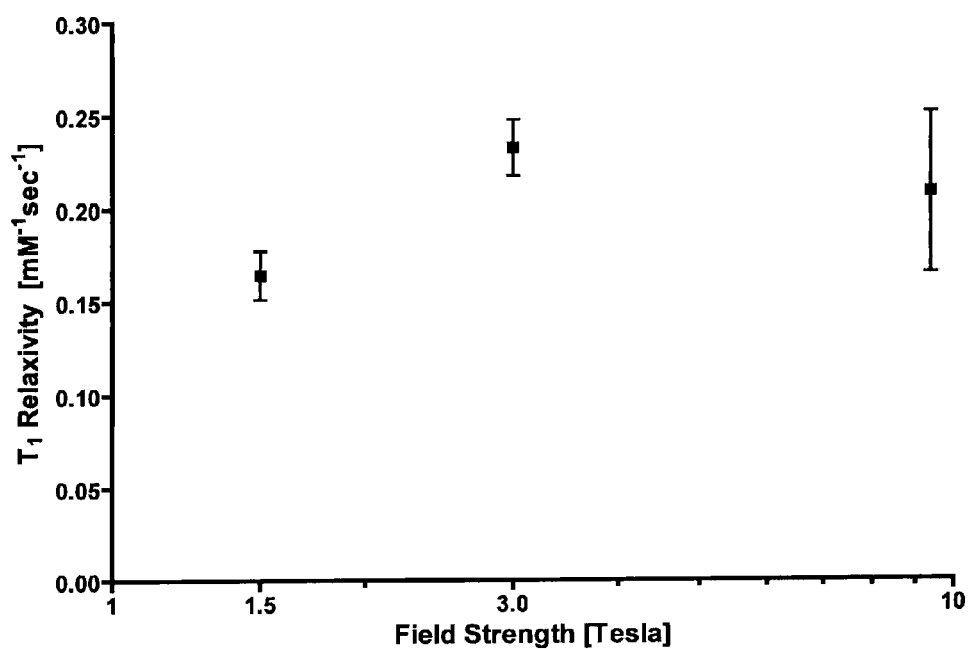
FIG. 4 shows the longitudinal relaxivity of buffered saline solutions of Mito-CP at various magnetic field strengths.

The longitudinal relaxivity (R1) for buffered saline solutions of Mito-CP at various field strengths matched previous published values for other nitroxides, R1≈0.2 mM$^{-1}$ sec$^{-1}$. FIG. 4 depicts slight field dependence such that the relaxivity increased with field strength. At 1.5 T, 3.0 T, and 9.4 T Mito-CP exhibited an R1=0.1643±0.01314, 0.2322±0.0151, and 0.2083±0.0431 mM$^{-1}$ sec$^{-1}$, respectively. In addition to these measurements, CP was found to exhibit an R1=0.1546±0.00567 mM$^{-1}$ sec$^{-1}$ at 3.0 T, slightly less than its counterpart.

Example 4

In Vitro Localization of Mito-CP in Mitochondria: MRI Analysis

The experiment was carried out on a Signa 3.0 T GE scanner (GE, Waukesha, Wis.) using a custom quadrature rf coil with a G10 fiberglass vial rack. Rabbit heart mitochondria were isolated. For verification of MR detectable mitochondrial accumulation of Mito-CP, isolated rabbit mitochondria were separated into three eppendorf tubes each containing 40 μL of 15 mg/ml mitochondria. Six eppendorf tubes were prepared as indicated in Table 1 below (1-6), and three additional eppendorf tubes were prepared from the supernatant of tubes 4-6 (4b-6b):

TABLE 1

| Eppendorf Tube | Label | Contents |
|---|---|---|
| 1 | Buffer | 20 uL 0.1 M succinate<br>180 uL DPBS |
| 2 | Buffer + 10 uM Mito-CP | 20 uL 0.1 M succinate<br>180 uL DPBS<br>1.0 uL 2 mM Mito-CP/EtOH |
| 3 | Buffer + 10 uM CP | 20 uL 0.1 M succinate<br>180 uL DPBS<br>1.0 uL 2 mM CP/EtOH |
| 4 | Mitochondria | 40 uL 15 mg/mL mitochondria<br>20 uL 0.1 M succinate<br>140 uL DPBS |
| 5 | Mitochondria + 10 uM Mito-CP | 40 uL 15 mg/mL mitochondria<br>20 uL 0.1 M succinate<br>139 uL DPBS<br>1.0 uL 2.0 mM Mito-CP/EtOH |
| 6 | Mitchondria + 10 uM CP | 40 uL 15 mg/mL mitochondria<br>20 uL 0.1 M succinate<br>139 uL DPBS<br>1.0 uL 2.0 mM CP/EtOH |
| 4b | Supernatant #4 | |
| 5b | Supernatant #5 | |
| 6b | Supernatant #6 | |

Note that succinate is needed to activate the mitochondrial respiratory chain, necessary for normal function. All tubes were incubated at 37° C. for 10 minutes. Immediately following incubation, all tubes were centrifuged at 1,000×g for 4 minutes at 4° C. The supernatant was then transferred into another eppendorf tube. The mitochondria in tubes 4-6 were re-suspended with the addition of 50 mL of DPBS and allowed to settle naturally. All tubes were simultaneously imaged using a fast spin echo inversion recovery sequence (T$_E$=24.25 msec, T$_R$=15,000 msec, and an echo train of 16) at various inversion times for initial estimates of T$_1$ and a standard spin echo sequence (T$_E$=21 msec, T$_R$=15,000 msec) at various inversion times (T$_1$=63, 250, 500, 750, 1000, 1200, 1250, 1275, 1300, 1325,1350, 1375, 1400, 1450, 1600, 1700, 1750, 1800, 1850, 1900, 2500, 3000, 3500, 4000 msec). T$_1$ maps were then generated from the spin echo inversion recovery data.

To determine the specificity that Mito-CP has toward mitochondria, the compound carboxy-proxyl (CP) was used for comparison. CP is a 5-member nitroxide ring, depicted in FIG. 1, without the ten chain linking carbons and the triphenylphosphonium. CP is known to be impermeable to lipid membranes but remains detectable by both MR and EPR. These properties make CP an ideal control for specificity of Mito-CP toward mitochondria.

Figure 5:
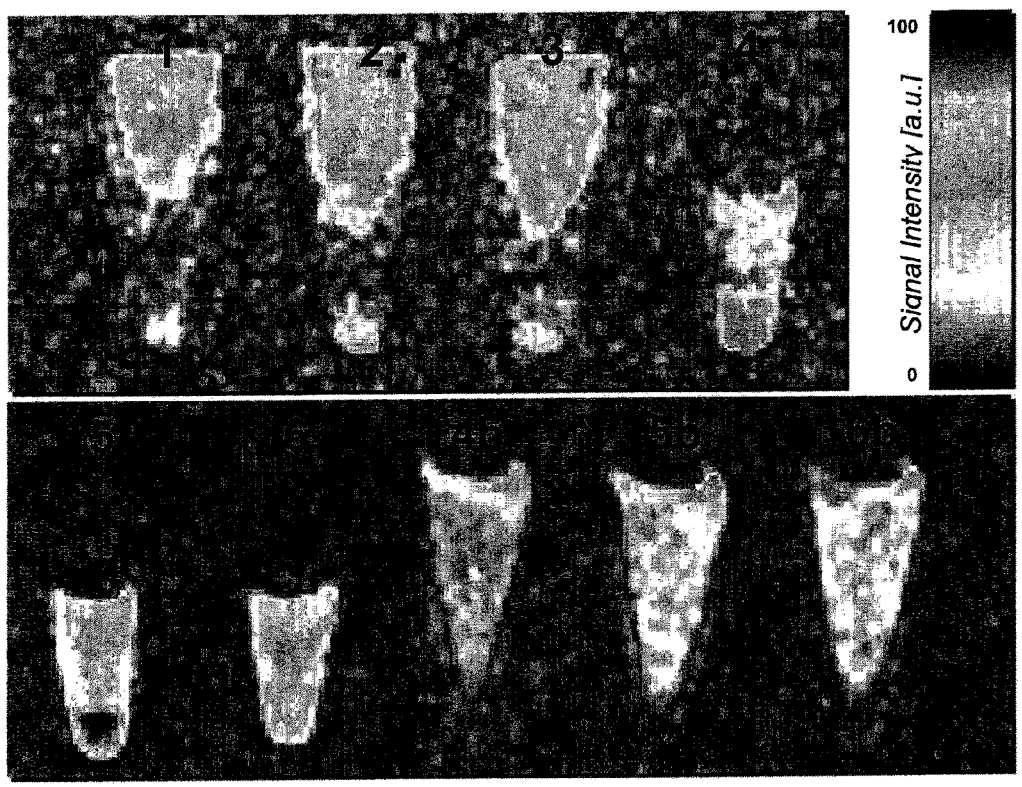
FIG. 5 shows spin echo inversion recovery images (TI=1900 msec) of the eppendorf tubes containing mixtures described in Table 1.

FIG. 5 depicts T1 weighted images of cross-sections through the nine eppendorf tubes at the inversion time of 1900 msec. The overlaid numbers correspond to the labels from Table 1. Within several minutes after the mitochondria were re-suspended in solution (tube 4-6), settling was observed that also confirmed with imaging as a differences in contrast at the bottom of the eppendorf tubes containing mitochondria. The mitochondria treated with the Mito-CP (tube 5) were found to have an shortened T$_1$, indicating uptake. The mitochondria treated with CP (tube 6) did not enhance considerably compared to mitochondria alone (tube 4) demonstrating the selectivity of Mito-CP for uptake into mitochondria. No observed differences were found in the supernatant. These results suggest the presence of an increased concentration within the mitochondria compared to the incubating solution demonstrating the ability of Mito-CP to indirectly visualize the presences of mitochondria.

Results from the isolated rabbit mitochondria demonstrated a clear uptake of Mito-CP. Ignoring partial voluming and assuming a similar hydration sphere as in free water, an estimated mitochondrial associated Mito-CP tissue concentration of 0.143 mM can be calculated using the estimated longitudinal tissue relaxivity and the longitudinal relaxation time from the untreated mitochondria. This would suggest at least a 140-fold increase in concentration within the mitochondria compared to the incubating solution.

Example 5

In Vivo Systemic Concentration—EPR

In order to determine nitroxide accumulation and elimination rates, in vivo systemic blood concentration was determined using EPR and in vivo tumor concentration was determined using MRI. One male Fisher rat (345 g) and six male Sprague-Dawley rats (240-370 g) were anesthetized with 1.2 mg/kg urethane. Using polyethylene tubing (PE50), femoral vein and arterial catheters were placed. To reduce clotting 400 units/kg heparin was administer intravenously. For high arterial blood pressure, the PE50 tubing was advanced into the descending aorta. The PE50 tubing was then run through the X-band electron paramagnetic resonance (EPR) resonator and connected to the venous catheter using a poly vinyl chloride (PVC) couple creating an arterial-venous (AV) shunt. This allowed for the continuous sampling of the in vivo Mito- CP blood concentration. Various doses of Mito-CP and CP were administered via a tail-vein catheter. Following each injection, EPR spectra were collected every 86 seconds for at least 30 minutes. In order to determine if Mito-CP or CP was reduced or eliminated, the blood remaining within the PE50 tubing from the rats treated with 9 mmol/kg was removed and treated with 10 uL ferricyanide following the last acquisition of EPR spectra and an additional spectrum was obtained. Ferricyanide, $(Fe(CN)_6)^{3-}$, will oxidize the reduced nitroxide (i.e. hydroxylamine) back to the original nitroxide. Rectal temperature was monitored and maintained at 37±1° C.

Figure 6:
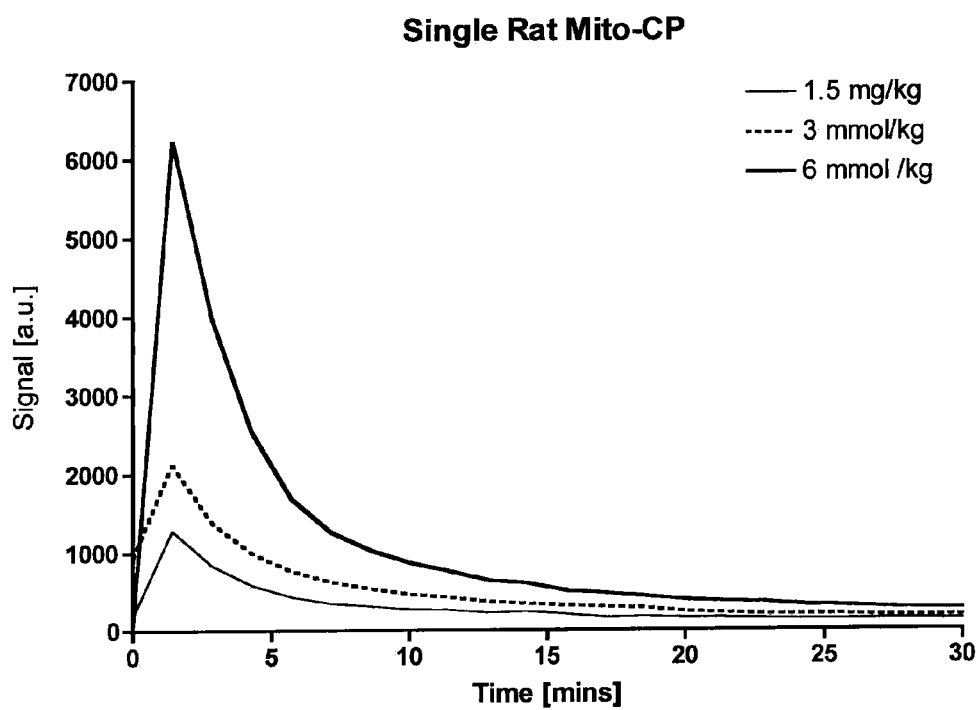
FIG. 6 shows transient in vivo Mito-CP blood concentration curves obtained from a single rat. Data were obtained at X-band EPR using a femoral arterial-venous shunt catheter (PE50 tubing) that allowed for repeated sampling (every 86 s) of the EPR spectrum. Subsequent injections were collected in order of increasing concentration and were spaced at least 1 hour apart.

Depicted in FIG. 6, are the transient in vivo Mito-CP blood concentration curves obtained from a single rat using a femoral arterial-venous shunt catheter that allowed for repeated sampling (every 86 s) of the X-band EPR spectrum. Fitting these curves to a monoexponential decay following the peak of the curve suggests that Mito-CP has an in vivo half-life of approximately 2 minutes.

Figure 7:
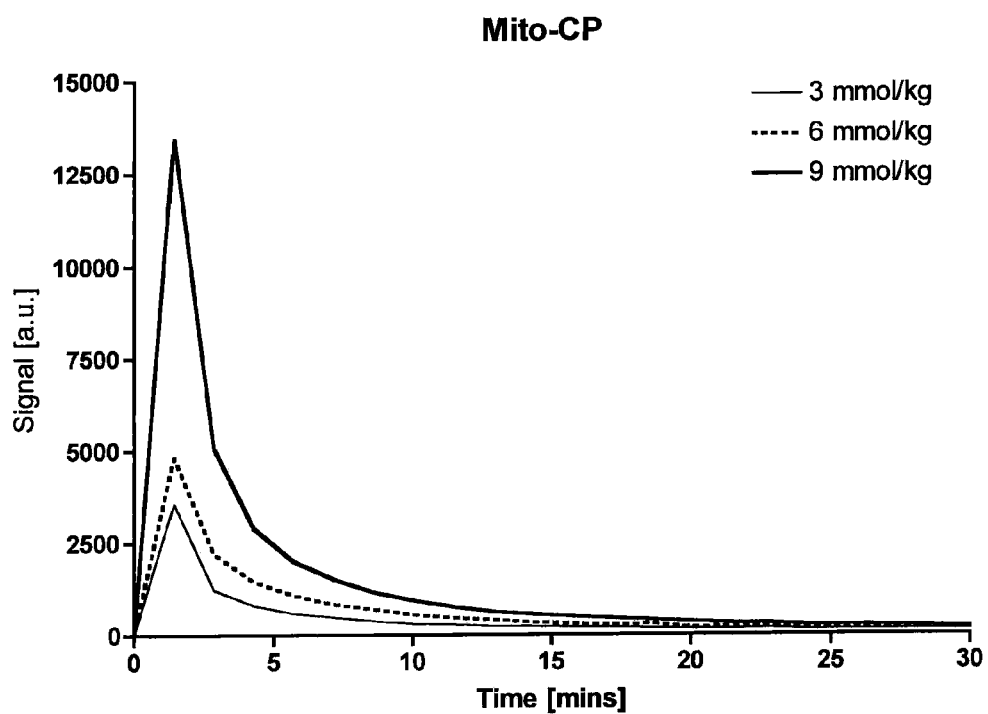
FIG. 7 shows transient in vivo Mito-CP blood concentration curves obtained from separate individual rats. Data were obtained at X-band EPR using femoral arterial-venous shunt catheter that allowed for repeated sampling (every 86 s) of the EPR spectrum. Note that the Mito-CP was eliminated from the blood within 30 minutes.
Figure 8:
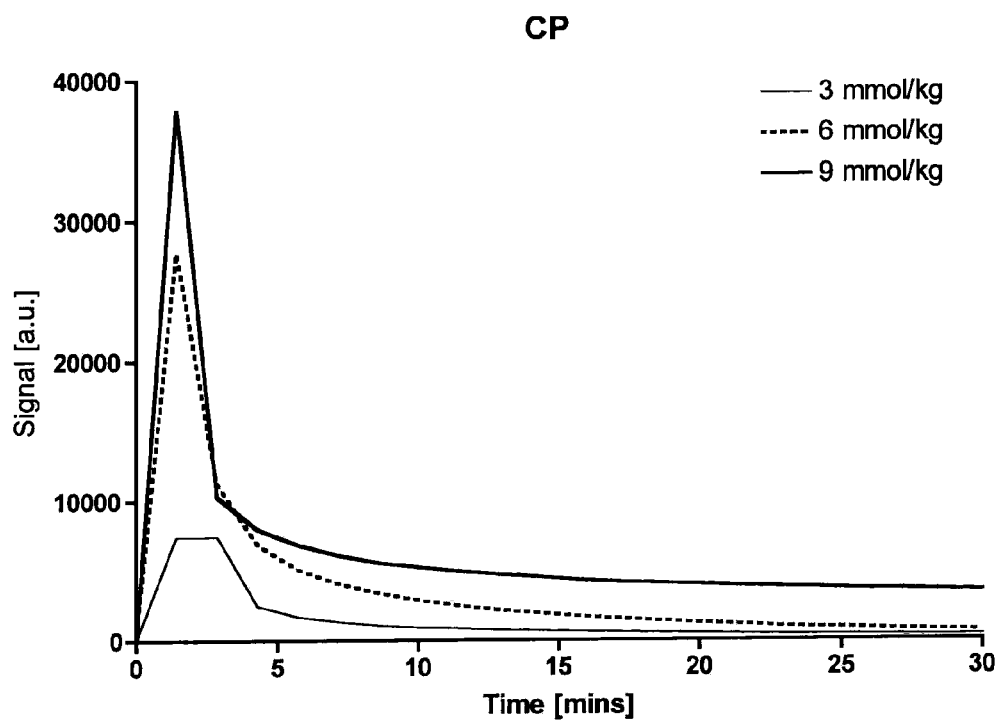
FIG. 8 shows transient in vivo CP blood concentration curves obtained from separate individual rats. Data were obtained at X-band EPR using femoral arterial-venous shunt catheter that allowed for repeated sampling (every 86 s) of the EPR spectrum. Note that the CP concentration had significantly slower elimination rates than the Mito-CP counterpart suggesting that the Mito-CP was not only being reduced but also was being taken up by tissue.

The transient in vivo Mito-CP and CP blood concentration curves obtained from independent rats using femoral arterial-venous shunt are displayed in FIGS. 7 and 8, respectively. Nitroxides are rapidly reduced in vivo by the reduction capacity within blood. Mito-CP was almost completely eliminated/reduced from the blood within 30 minutes following the bolus injection. However, the CP concentration had significantly slower elimination/reduction rates than at the respective Mito-CP concentration suggesting that the Mito-CP was not only being reduced but also was being taken up by tissue. At the dose of 9 mmol/kg, CP was still detectable within the systemic circulation while Mito-CP was not.

Figure 9:
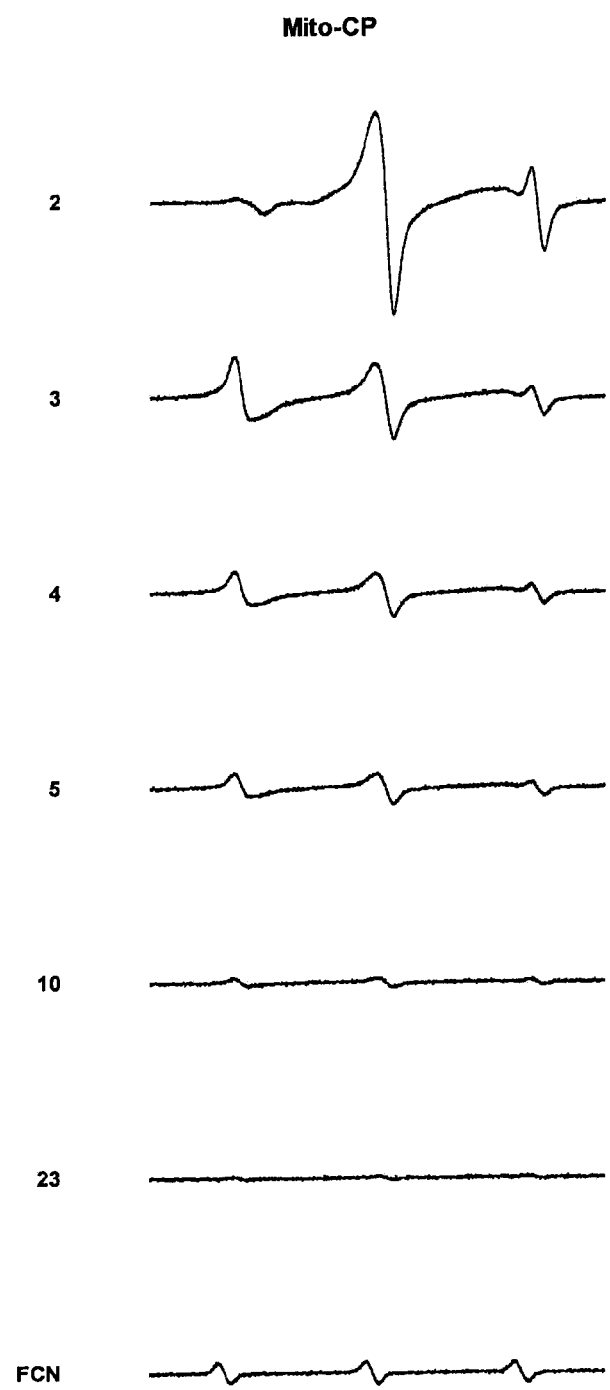
FIG. 9 shows transient in vivo Mito-CP blood X-Band EPR spectra obtained from a single rat using the AV-shunt at various time points. Following the acquisition of the dynamic EPR spectra, the blood within the catheter was treated with $(Fe(CN_6))^{3-}$ to reverse the reduction of Mito-CP. The Mito-CP signal was recovered following treatment with $(Fe(CN_6))^{3-}$, labeled as FCN.
Figure 10:
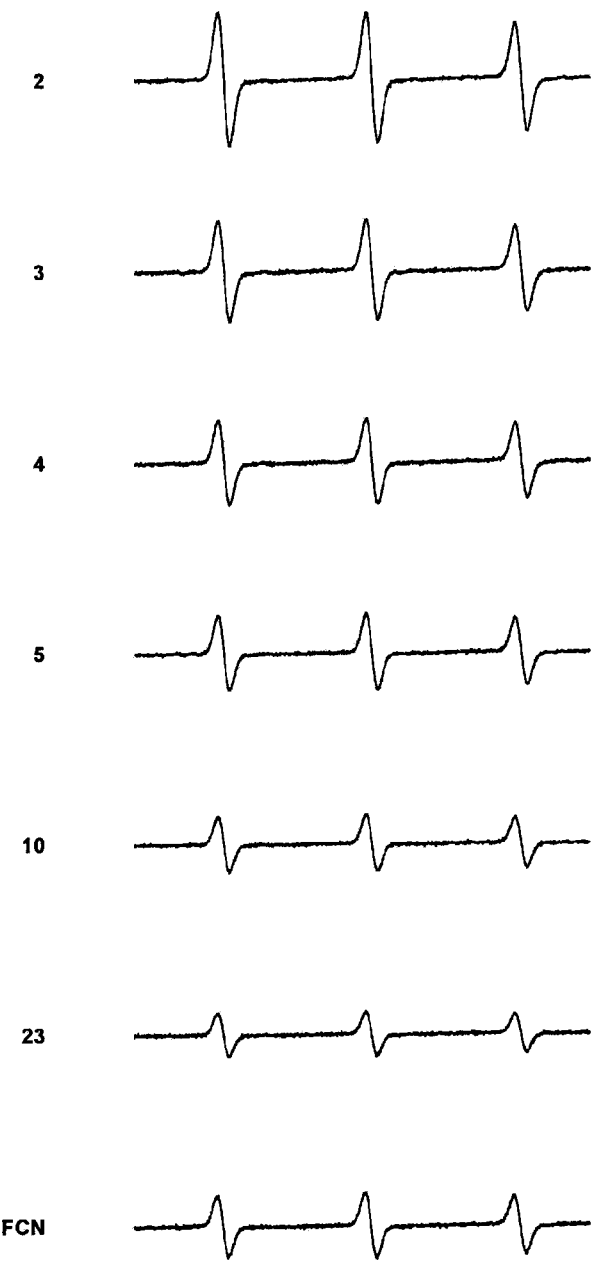
FIG. 10 shows transient in vivo CP blood X-Band EPR spectra obtained from a single rat using the AV-shunt at various time points. Following the acquisition of the dynamic EPR spectra, the blood within the catheter was treated with $(Fe(CN_6))^{3-}$, labeled as FCN, to reverse the reduction of CP. Like Mito-CP, the CP signal was recovered following treatment with $(Fe(CN_6))^{3-}$ but not back to its initial level. Both Mito-CP and CP had similar increases in signal following treatment with $(Fe(CN_6))^{3-}$.

The transient in vivo Mito-CP and CP blood EPR spectra obtained from one rat using the AV-shunt at various time points are present in FIGS. 9 and 10, respectively. Following the acquisition of the dynamic EPR spectra, the blood within the catheter was treated with ferricyanide to reverse the reduction of CP. Both Mito-CP and CP had similar increases in signal following treatment with ferricyanide. Since, Mito-CP did not have super-reduction compared to CP this further suggest that Mito-CP undergoes tissue absorption in addition to in vivo reduction.

Example 6

In Vivo MRI

A female Fisher rat weighing 162 g was anesthetized with 75 mg/kg ketamine, 10 mg/kg xylazine and 2.5 mg/kg acepromazine and inoculated with the Mat B III cell line (ATCC #CRL-1666). The Mat B III cell line is a rapidly growing, well vascularized, rat mammary adenocarcinoma. Fourteen days post inoculation the rat was anesthetized with 1.2 mg/kg urethane. Two minutes into a dynamic time series of T1-weighted SPGR images (TE=3 ms, TR=78.125, Effective TR=10 seconds, Repetitions=150, Slice thickness=1 mm, flip angle=30, slices=8) 4 mg/kg Mito-CP with 1% DMSO vehicle in 0.25 mL of PBS was injected via the tail-vein. Both pre- and post-contrast T1-weighted images were obtained.

Figure 11:
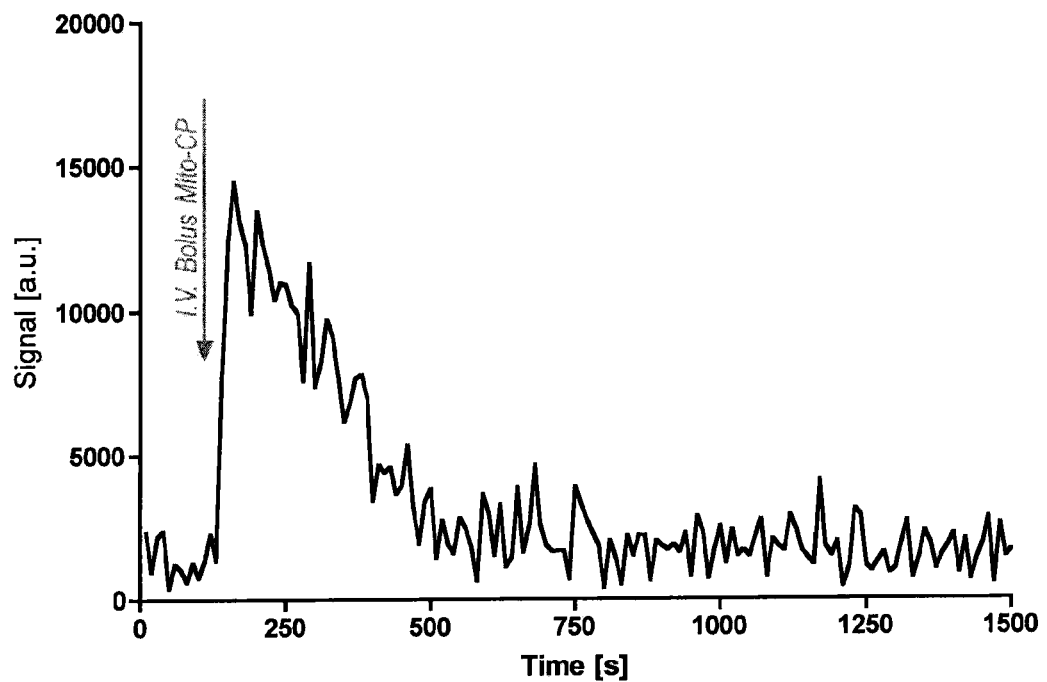
FIG. 11 shows the dynamic time series of a representative voxel from T1-weighted SPGR images obtained in regions of aggressive breast tumor.

A representative dynamic T1-weighted time course obtained from breast tumor shown in FIG. 11. The longer duration of the tissue time curve compared to the blood concentration time curve suggests uptake of the contrast agent by the aggressive breast tumor. Results from a monoexponential fit of the dynamic T1-weighted time course revealed tissue decay constants ranging from 100 to 500 s.

Figure 12:
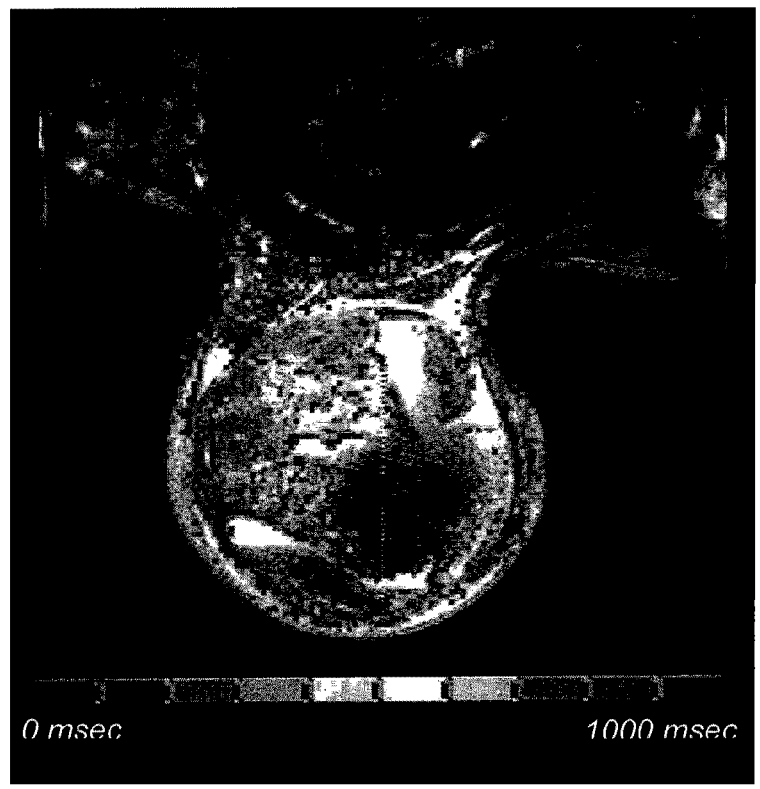
FIG. 12 is a Mito-CP decay map (fit $\alpha$=0.05).

A decay map showing exponential MR signal decay rates overlaid on a post-contrast T1-weighted image of a highly necrotic breast tumor is depicted in FIG. 12. The aggressive rim of the tumor matches regions of MR signal decay due to nitroxide reduction. Necrotic regions of the tumor lack nitroxide decay. Necrotic regions were confirmed by gross dissection follow euthanasia.

Example 7

In vivo Mitochondrial Labeling using Mito-Gd-DOTA Enhanced Magnetic Resonance Imaging This example demonstrates the feasibility of using an exemplary mitochondria target gadolinium chelate complex, Mito-Gd-DOTA (see FIG. 14), as an in vivo contrast agent.

Preliminary data from a SD rat with a C6 glioma (brain tumor) at 21 days post inoculation. FIG. 15A shows the uptake of Mito-Gd-DOTA within the tumor as a time series. Each time point represents ten seconds. The Mito-Gd-DOTA agent is taken up by the tumor slowly over time. Although similar general patterns are seen with standard Gd-DOTA, the uptake is significantly different than with standard Gd-DOTA.

FIG. 15B shows post contrast images taken 40 minutes after injection with the Mito-Gd-DOTA agent. Agent uptake can be seen in the right hemisphere corresponding to the area of tumor inoculation.

Example 8

Chemical Synthesis of Two Novel Mitochondria Targeting Contrast Agents: Mito-Gd-DOTA and Mito-Gd-DTPA Materials and Methods. All the materials and solvents were obtained from Sigma-Aldrich (Milwaukee, Wis.) and used without further purification unless otherwise noted. S-2-(4-Isothiocyanatobenzyl)-1,4,7,10-tetraazacyclododecane-tetraacetic acid (p-SCN-Bn-DOTA, 1) and 2-(4-Isothiocyanatobenzyl)-diethylenetriaminepentaacetic acid (p-SCN-Bn-DTPA) were purchased from Macrocyclics (Dallas, Tex.). Characterization was performed on HPLC and HRMS for all products. HPLC experiments were performed using an Agilent 1100 system equipped with UV-Vis absorption and fluorescence detectors using a C18 column (Alltech, Kromasil, 250×4.6 mm, 5 mm) that was equilibrated with 10% CH3CN (containing 0.1% (v/v) trifluoroacetic acid (TFA)) in 0.1% TFA aqueous solution. Mass spectra were obtained using a 7.0 Tesla Fourier Transform Ion Cyclotron Resonance (FTICR) Mass Spectrometer.

Synthesis of Mito-Gd-DOTA and Mito-Gd-DTPA. Both compounds, Mito-Gd-DOTA (FIG. 16-4) and Mito-Gd-DTPA, were synthesized according the synthetic route shown in FIG. 16. (10-aminodecyl)triphenylphosphonium bromide (FIG. 16-3) was synthesized and prepared as previously described. Briefly, a mixture containing (10-bromodecyl)phthalimide (7 g, 0.019 mol) and triphenylphosphine (5 g, 0.019 mol) in acetonitrile (60 mL) was refluxed for 15 hours. The solvent distilled under reduced pressure. Purification of the crude product by flash chromatography on a silica gel ($CH_2Cl_2$/EtOH 80:20) afforded a white solid 10-decylphthalimidyl triphenylphosphonium bromide (9 g, 73%). The calculated MS value for $[C_{36}H_{39}NO_2P]^+$, $Br^-$; $[C_{36}H_{39}NO_2P]^+$ is 548.3. the product's MS value was 548.3. To prepare the (10-aminodecyl)triphenylphosphonium bromide (FIG. 16-3), hydrazine was added (0.54 mL, 0.0108 mol) to a solution of (10-decylphthalimidyl)triphenylphosphonium bromide (7 g, 0.0108 mol) in EtOH (70 mL). The mixture was refluxed for 15 hours. The solvent was removed under reduced pressure and the impurity was crystallized using a mixture $Et_2O$/EtOH (100 mL+45 mL). The product was purified by flash chromatography on a silica gel ($CH_2Cl_2$/EtOH 80:20) afforded a yellow solid (4 g, 73%). The calculated HRMS for $[C_{28}H_{37}NP]^+$, $Br^-$; $[C_{28}H_{37}NP]^+$ is 418.2. The product's measured HRMS value was 418.2.

Figure 16:
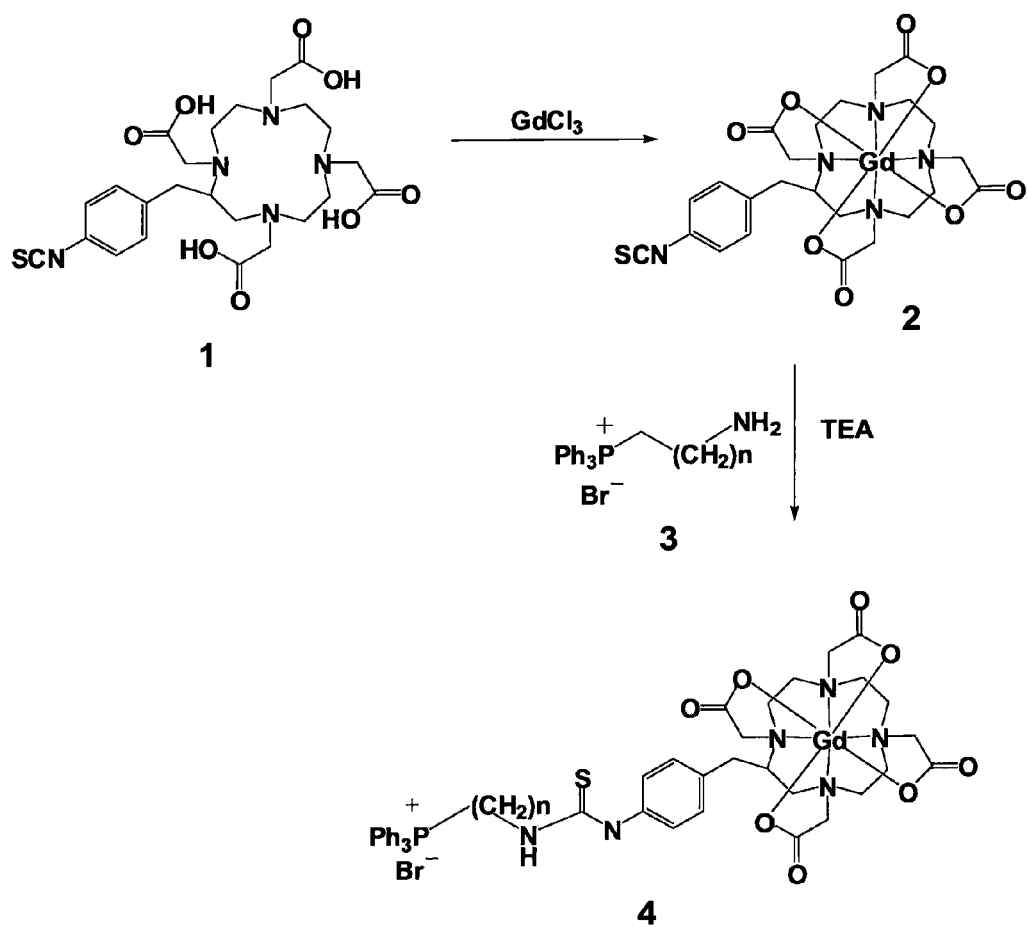
FIG. 16 depicts the scheme for the chemical synthesis of the contrast agent Mito-Gd-DOTA.

Synthesis of ρ-SCN-Bn-Gd-DOTA (FIG. 16-2). To a stirred solution of the free ligand (FIG. 16-1) (50 mg), in ddH$_2$O (3 ml), GdCl$_3$ (100 mg) was added. The pH of the solution was monitored and kept between 6.0 and 7.0 using 0.1 M NaOH. The reaction was stirred overnight and monitored by HPLC until the total disappearance of the free ligand (FIG. 16-1) peak was observed. Purification of the crude product by preparative HPLC using a C18 column afforded a white powder (0.0606 g, 95%), corresponding to ρ-SCN-Bn-Gd-DOTA (FIG. 16-2). The calculated HRMS for $C_{24}H_{29}GdN_5O_8S$, $[C_{24}H_{29}GdN_5O_8S]+$ is 704.8308. The product's measured HRMS value was 705.1130. ρ-SCN-Bn-Gd-DTPA was synthesized using the same procedure (data not shown).

Figure 17:
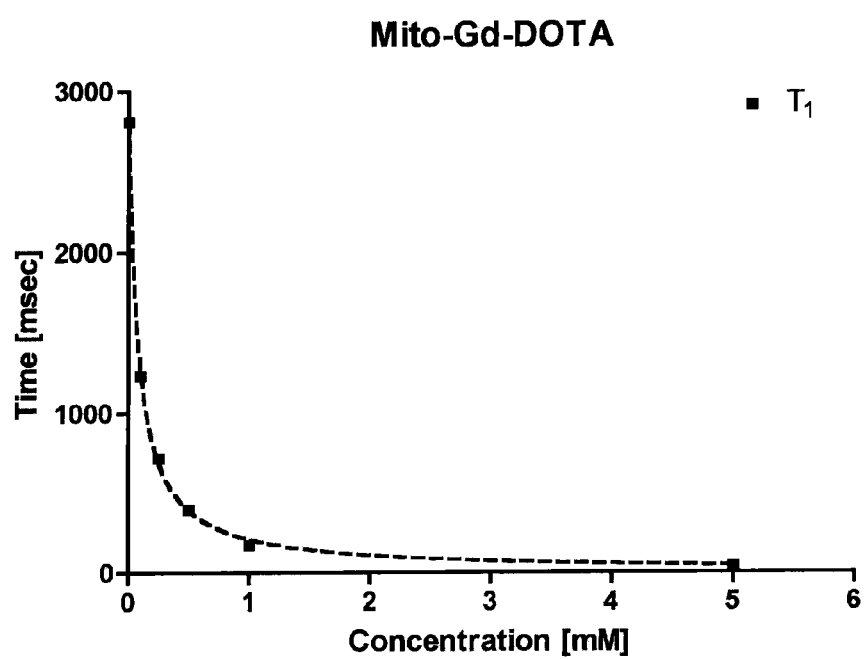
FIG. 17 depicts a relaxivity study of Mito-Gd-DOTA at 9.4 T.

Synthesis of Mito-Gd-DOTA. To an argon purged solution of ρ-SCN-Bn-Gd-DOTA (FIG. 16-2) (0.03 g, 0.0425 mmol) and (10-aminodecyl)triphenylphosphonium bromide (FIG. 16-3) (0.025 g, 0.05 mmol) in anhydrous DMSO (25 mL), (0.014 g, 0.143 mmol) of TEA were added. The mixture was allowed to react overnight and monitored by HPLC. Purification of the crude product by preparative HPLC using a C18 column afforded a white powder (0.0455 g, 93%), corresponding to (FIG. 16-4). The calculated HRMS value for $C_{52}H_{66}GdN_6O_8PS+$, $[C_{52}H_{66}GdN_6O_8PS]+$ is 1123.3636. The product's measured HRMS value was 1124.5301. FIG. 17 illustrates a relaxitivity study of Mito-Gd-DOTA at 9.4 T. The DTPA derivative was synthesized using substantially the same procedure (data not shown).

The present invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

What is claimed is:

1. The mitochondria-targeted contrast agent molecule, wherein the mitochondria-targeted contrast agent molecule is Mito-Gd-DOTA having the structure:

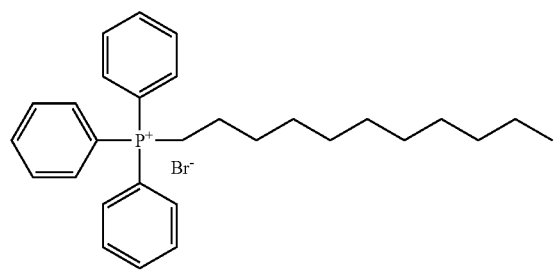

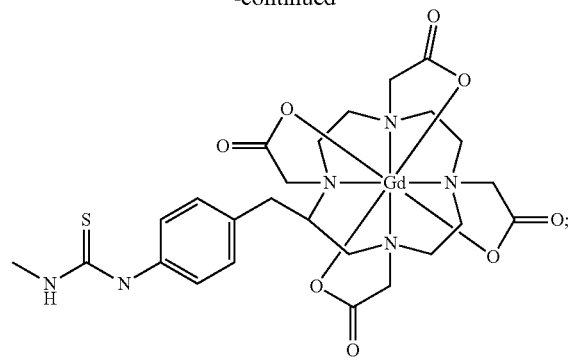

or Mito-Gd-DTPA having the structure:

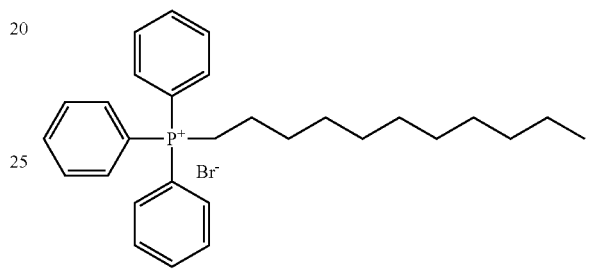

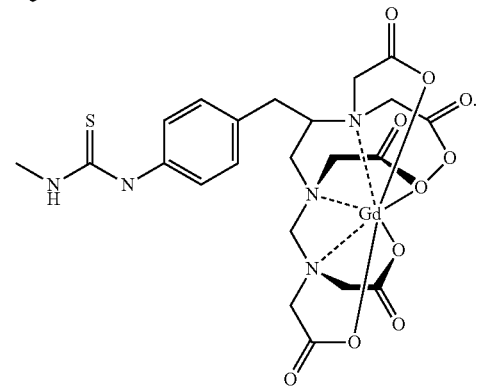

2. A method of in vivo MR imaging a target area of a subject comprising the steps of:
   a) administering a compound according to claim 1 to the subject;
   b) applying a pulse sequence selected to acquire MR imaging data from the target area of the subject; and
   c) reconstructing an image of the target area of the subject having enhanced contrast in areas of at least one of metabolic and mitotic activity.

* * * * *